US006721046B1

(12) United States Patent
Halliyal et al.

(10) Patent No.: US 6,721,046 B1
(45) Date of Patent: Apr. 13, 2004

(54) MONITORING OF CONCENTRATION OF NITROGEN IN NITRIDED GATE OXIDES, AND GATE OXIDE INTERFACES

(75) Inventors: Arvind Halliyal, Sunnyvale, CA (US); Bhanwar Singh, Morgan Hill, CA (US); Ramkumar Subramanian, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 240 days.

(21) Appl. No.: 09/903,885

(22) Filed: Jul. 12, 2001

(51) Int. Cl.$^7$ ............................................... G01B 11/00
(52) U.S. Cl. .................. 356/237.5; 438/16; 324/158.1; 356/239.7
(58) Field of Search .......................... 356/239.7, 239.8, 356/237.2–237.5, 600, 630–632; 250/559.27; 324/752, 765, 158.1; 438/263, 786, 514, 14–18, 769; 702/181; 700/108, 109, 121

(56) References Cited

U.S. PATENT DOCUMENTS 6,124,178 A * 9/2000 Sung et al. .................. 438/308
6,561,706 B2 * 5/2003 Singh et al. ................. 396/611

OTHER PUBLICATIONS

Niu, X., et al., "*Specular Spectroscopic Scatterometry in DUV Lithography,*" Timbre Technology, Inc., et al.
Smith, T., et al., "*Process Control in the Semiconductor Industry,*" http://www–mtl.mit.edu/taber/Research/Process Control/IERC99/ pp. 1–24.
Cote, D.R., et al., "*Plasma–assisted chemical vapor deposition of dielectric thin films for ULSI semiconductor circuits,*" IBM Journal of Research & Development, vol. 43, No. ½ pp. 1–30.

* cited by examiner

Primary Examiner—Richard A. Rosenberger
Assistant Examiner—Vincent P. Barth
(74) Attorney, Agent, or Firm—Amin & Turocy, LLP

(57) ABSTRACT

A system for regulating nitrided gate oxide layer formation is provided. The system includes one or more light sources, each light source directing light to one or more nitrided gate oxide layers being deposited and/or formed on a wafer. Light reflected from the nitrided gate oxide layers is collected by a measuring system, which processes the collected light. The collected light is indicative of the nitrogen concentration of the respective nitrided gate oxide layers on the wafer. The measuring system provides nitrogen concentration related data to a processor that determines the nitrogen concentration of the respective nitrided gate oxide layers on the wafer. The system also includes one or more nitrided gate oxide layer formers where a nitride gate oxide former corresponds to a respective portion of the wafer and provides for nitrided gate oxide layer formation thereon. The processor selectively controls the nitrided gate oxide layer formers to regulate nitrided gate oxide layer formation on the respective nitrided gate oxide layer formations on the wafer, and particularly to control, in situ, the amount of nitrogen incorporated into the gate oxide layer.

19 Claims, 14 Drawing Sheets

Prior Art Fig. 1

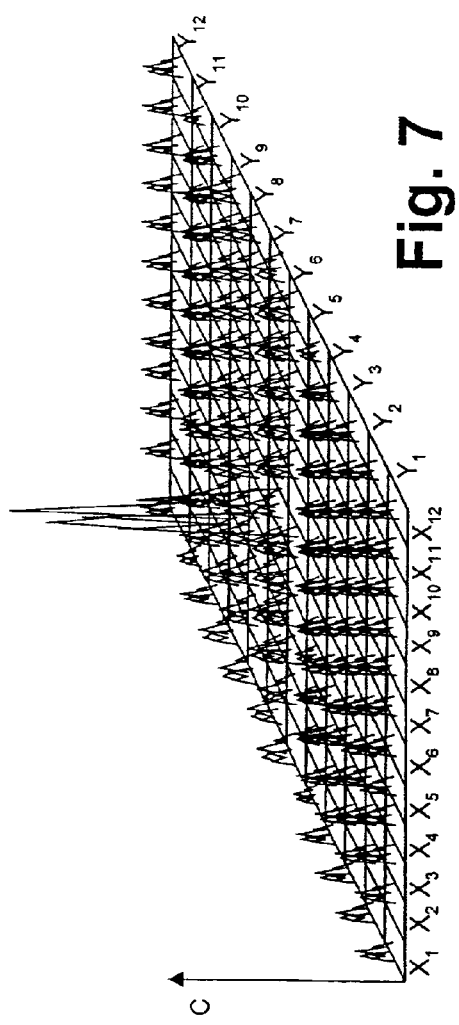
Fig. 8
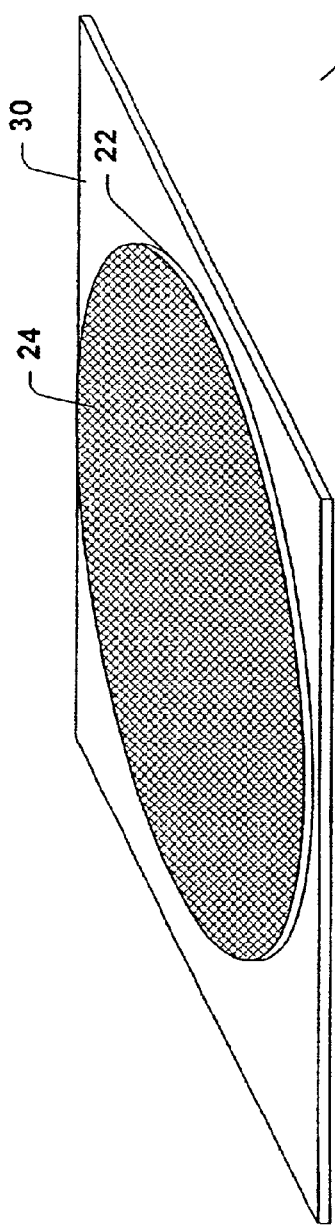
Fig. 6
Fig. 7

MONITORING OF CONCENTRATION OF NITROGEN IN NITRIDED GATE OXIDES, AND GATE OXIDE INTERFACES

TECHNICAL FIELD

The present invention generally relates to semiconductor processing, and in particular to systems and methods for monitoring and regulating the concentration of nitrogen in a nitrided gate oxide layer.

BACKGROUND OF THE INVENTION

In the semiconductor industry, there is a continuing trend toward manufacturing integrated circuits with a greater number of layers and with higher device densities. To achieve these high densities there have been, and continue to be, efforts towards reducing the thickness of layers, improving the uniformity of layers, reducing the thickness of devices and scaling down device dimensions (e.g., at sub micron levels) on semiconductor wafers. In order to accomplish higher device packing densities, thinner layers, more uniform layers, smaller feature sizes, and smaller separations between features are required. This can include the width and/or thickness of gate oxide materials, (e.g., silicon oxide, silicon nitride, silicon oxynitride, high K metal oxides), interconnecting lines, spacing and diameter of contact holes, and the surface geometry such as corners and edges of various features.

But as lateral device dimensions are scaled deeply into the sub-micron range, as required to achieve desired speed and integration improvements, corresponding reductions in gate-oxide thickness can have undesired impacts. For example, problems associated with direct tunneling can occur when gate oxide thickness decreases below certain thresholds. For example, as the gate oxide thickness is reduced into the sub-two nanometer region, a rapid increase in direct tunneling and boron penetration in PMOS devices can be a major obstacle for device scaling.

The process of manufacturing semiconductors, or integrated circuits (commonly called ICs, or chips), typically consists of more than a hundred steps, during which hundreds of copies of an integrated circuit can be formed on a single wafer. Generally, the process involves creating several layers on and/or in a substrate that ultimately forms the complete integrated circuit. This layering process can create electrically active regions in and/or on the semiconductor wafer surface. Insulation and conductivity between such electrically active regions can be important to reliable operation of such integrated circuits. Thus, controlling the width and/or uniformity of layers created during the layering process can be important to the reliable operation of such integrated circuits. Further, the insulating and/or conducting properties of a layer can be affected by the chemical composition of a layer (e.g., the concentration of one or more elements). One type of integrated circuit in which insulation and conductivity between electrically active regions is important is electronic memory.

Electronic memory comes in different forms to serve different purposes. One such electronic memory, flash memory can be employed for information storage in devices including, but not limited to, voice recorders, cellular phones, digital cameras and home video game consoles. Flash memory can be considered a solid-state storage device, in that functionality is achieved electronically rather than mechanically. Flash memory is a type of EEPROM (Electrically Erasable Programmable Read Only Memory) chip. Flash memories are a type of non-volatile memory (NVM). NVMs can retain information when power to the NVM is removed in contrast to NVMs with volatile memories (e.g., DRAM, SRAM) that lose stored data when power is removed. Flash memory is electrically erasable and re-programmable in-system. The combination of non-volatility and in-system eraseability/re-programmability make flash memory well-suited to a number of end-product applications including, but not limited to, personal computer BIOS, telecom switches, cellular phones, internetworking devices, instrumentation, automotive devices and consumer-oriented voice, image and data storage devices (e.g., digital cameras, digital voice recorders, PDAs).

An exemplary MOSFET 100 (Metal Oxide Semiconductor Field Effect Transistor), another semiconductor device, is illustrated in Prior Art. FIG. 1. The exemplary MOSFET device 100 illustrated includes a gate 104 separated from a substrate 110 by a gate oxide 102. The MOSFET includes a source 106 and a drain 108. The components of the thin gate oxide 102 can be important to reliable operation of the MOSFET 100, and thus, manufacturing the gate oxide 102 with desired components to precise measurements facilitates increasing MOSFET reliability.

The gate oxide layer 102 functions as an insulating layer. The gate oxide layer 102 can be the smallest feature of a device. Controlling the components of the gate oxide layer 102 can contribute to increasing the switching speed of a transistor. Thus, precisely monitoring and controlling properties of the gate oxide layer 102 including, but not limited to, relative material concentration, are important to facilitating reliable operation of the MOSFET 100. For example, the ability to store data, to retain data, to be erased, to be reprogrammed and to operate in desired electrical and temperature ranges can be affected by the components that constitute the gate oxide layer 102.

In deep submicron CMOS technology to improve the reliability of ultra-thin gate oxides and also to prevent boron penetration from the poly gate, different nitridation techniques are used to incorporate nitrogen into gate oxides. Nitridation can be done by in situ or post annealing of oxides in an ambient of nitric oxide (NO), nitrous oxide, or ammonia. Alternate techniques include implanting nitrogen into the gate oxides. The nitridation process can be done in batch type furnace or in a single wafer processing cluster tool. Stacked gate oxides are also prepared by depositing a thin nitride layer on an oxide. Plasma nitridation techniques such as RPN (remote plasma nitridation) and DPN (decoupled plasma nitridation) are also employed for nitridation.

The insulating properties of the gate oxide layer 102 can be affected not only by its thickness but by the chemical composition of the gate oxide layer 102, including the concentration of nitrogen. Precisely controlling the gate oxide thickness and composition (such as nitrogen concentration) are required to maintain current levels required for circuit operation in devices employing a gate oxide layer 102.

Properties of the gate oxide layer 102 including, but not limited to, chemical composition (e.g., nitrogen concentration), thickness and uniformity can affect the operation of one or more MOSFETs fabricated on the gate oxide layer 102. It is to be appreciated that the present invention can be applied to the formation of gate oxide layers in other integrated circuits. For example, the present invention can be applied to all (for example in DRAM, SRAM, and other memory devices, microprocessors, logic circuits and tunnel oxides in EEPROM type flash memory devices and SONOS type flash memory devices) CMOS devices where thin nitrided gate oxides are used. The technique can also be applied to oxynitrides, or oxide/nitride type stacked gate oxides.

The requirement of small features with close spacing between adjacent features in semiconductor devices with submicron geometry requires sophisticated manufacturing techniques including precise control of gate oxide layer formation. By way of illustration, fabricating microprocessor or memory devices using such sophisticated techniques may involve a series of steps including the formation of layers/structures by chemical vapor deposition (CVD), rapid thermal oxidation and oxide growth. Conventionally, difficulties in forming ultra thin gate oxide layers, with precise nitrogen concentration, have limited the effectiveness and/or reliability of such devices manufactured by conventional techniques. By way of further illustration, for CMOS devices, similar gate oxide considerations can apply to at least two different portions of a gate dielectric structure: the Si—$SiO_2$ interface and the bulk of dielectric film. The Si—$SiO_2$ interfaces for CMOS devices may be formed by methods including, but not limited to, thermal oxidation of the Si substrate (wherein the Si—$SiO_2$ interface is continuously regenerated and buried beneath the surface of the Si wafer), ideal deposition processes (where the metallurgical boundary between the Si and the deposited $SiO_2$ film is maintained at the original surface of the Si), real deposition processes, (where plasma or thermally generated, chemically active oxygen species interact with the Si substrate during deposition to facilitate oxidation occurring at the Si substrate during initial deposition to displace the Si—$SiO_2$ interface into the bulk of the Si substrate layer) and by a two-step plasma oxidation/deposition (where a thin passivating layer of $SiO_2$ is created during a remote-plasma-assisted oxidation (RPAO) phase to form the interface and to prevent further oxidation of the Si substrate during oxide deposition by remote-plasma-enhanced chemical vapor deposition (RPECVD). After gate oxides are prepared by any these techniques, nitridation of gate oxide can be performed by any of the techniques described earlier to incorporate nitrogen into the gate oxide either at Si/$SiO_2$ interface or in the bulk of the gate oxide.

Due to the extremely fine structures that are fabricated in submicron CMOS devices (beyond 0.25 micron technology) controlling the formation of gate oxide materials used to form a gate oxide layer are significant factors in achieving desired critical dimensions and operating properties and thus in manufacturing reliable devices. The more precisely the gate oxide layer can be formed, including the more precisely the concentration of chemicals that contribute to a gate oxide equivalent thickness calculation can be controlled, the more precisely critical dimensions may be achieved, with a corresponding increase in reliability. Similarly, more precisely a gate oxide layer can be formed, including monitoring thickness and chemical concentration affecting equivalent thickness, the higher quality and more reliable CMOS devices can be fabricated.

Conventionally, due to non-uniform gate oxide layer formation and inaccurate gate oxide layer formation monitoring techniques, a thickness of gate oxide greater or lesser than the thickness desired may be formed. Similarly, due to inaccurate chemical composition monitoring, undesired concentrations of chemicals (such as concentration of nitrogen and oxygen) negatively affecting oxide equivalent thickness may be generated.

SUMMARY OF THE INVENTION

This section presents a simplified summary of the invention in order to provide a basic understanding of some aspects of the invention. This summary is not an extensive overview of the invention. It is not intended to identify key/critical elements of the invention nor is it intended to delineate the scope of the invention. Its sole purpose is to present some concepts of the invention in a simplified form as a prelude to the more detailed description that is presented later.

The present invention provides for a system that facilitates monitoring and controlling nitrided gate oxide layer formation. In particular, the present invention provides for monitoring the concentration of nitrogen (N) employed in nitriding a gate oxide layer to affect the equivalent gate oxide thickness of a nitrided gate oxide layer. Such nitrided gate oxide layers may be employed in devices including, but not limited to, microprocessors, logic devices, EEPROMs (e.g., flash memory), volatile memories (e.g., DRAM, SRAM) and other memory devices. The present invention is also applicable to gate oxides that employ high K metal oxides, where a thin nitrided layer is used as a top or bottom interface, and also to oxide/nitride gate stacks. An exemplary system may employ one or more light sources arranged to project light on one or more nitrided gate oxide layers on a wafer and one or more light sensing devices (e.g., photo detector, photo diode) for detecting light reflected by the one or more gate oxide layers. The light reflected from one or more nitrided gate oxide layers is indicative of at least nitrided gate oxide layer nitrogen concentration, which may vary during the gate oxide layer formation process.

One or more nitrided gate oxide layer formers can be arranged to correspond to a particular wafer portion. Each nitrided gate oxide layer former may be responsible for forming a nitrided gate oxide layer on one or more particular wafer portions. The nitrided gate oxide layer formers may be responsible for introducing nitrogen into the nitrided gate oxide layer. Precisely controlling the amount of nitrogen in the nitrided gate oxide layer can improve the performance of the nitrided gate oxide layer. Thus, the present invention facilitates precisely forming nitrided gate oxide layers that include precise concentrations of nitrogen, where the nitrogen concentration may be between one percent and ninety-nine percent nitrogen. The nitrided gate oxide layer more be formed by techniques including, but not limited to, chemical vapor deposition with nitrogen, growth over a thin oxide and annealing with nitrogen in the atmosphere. The nitrided gate oxide layer formers are selectively driven by the system to form a nitrided gate oxide layer on one or more particular wafer portions with a desired nitrogen concentration and/or a desired thickness and/or uniformity. The progress of the nitrided gate oxide layer formation is monitored by the system by comparing the concentration of chemicals affecting equivalent gate oxide thickness (e.g., nitrogen, silicon and/or oxygen) of the nitrided gate oxide layer on a wafer to a desired concentration. Different wafers and even different components within a wafer may benefit from varying nitrogen concentrations. Furthermore, the nitrided gate oxide layers may be involved in different nitridations of the nitrided gate oxides including, but not limited to, interfacial nitridation and top-surface nitridation. By monitoring nitrided gale oxide nitrogen concentration at one or more wafer portions, the present invention enables selective control of nitrided gate oxide formation. As a result, more optimal nitrided gate oxide formation is achieved, which in turn improves flash memory manufacturing. Similarly, such optimal nitrided gate oxide formation improves performance and reliability of other devices employing nitrided gate oxides (e.g., CMOS devices).

One particular aspect of the invention relates to a system for regulating nitrided gate oxide layer formation in submicron CMOS devices beyond 0.25 micron technology. The system includes a nitrided gate oxide former operative to form a nitrided gate oxide layer on a portion of a wafer. The nitrided gate oxide layer can be formed from materials including, but not limited to, silicon oxide, nitrogen, silicon nitride, and silicon oxynitride. The nitrided gate oxide layer can be of an oxide equivalent thickness down to less than three nanometers. Below the thickness of about two nanometers in an $SiO_2$ gate oxide film, direct tunneling becomes the dominant mechanism for current transport through the film. It is desirable for gate dielectric manufacturing to reduce direct tunneling while maintaining an oxide-equivalent thickness corresponding to a thinner $SiO_2$ film. Incorporating nitrogen into the gate oxide film can facilitate a reduction of leakage current of gate oxide.

The system also includes a nitrided gate oxide former driving system for driving a nitrided gate oxide former and a system for directing light on to a portion of the wafer. The system further includes a measuring system for measuring parameters of nitrided gate oxide formation nitrogen concentration based on light reflected from nitrided gate oxide formations and a processor that receives nitrided gate oxide formation nitrogen concentration data from the measuring system. The processor uses the data to generate feedback information that can be employed to base control of a nitrided gate oxide former so as to regulate nitrided gate oxide nitrogen concentration on the portion of the wafer.

Another aspect of the present invention provides a method for regulating nitrided gate oxide layer formation. The method includes defining a wafer as a plurality of portions and establishing one or more nitrided gate oxide layer formations to be formed in the one or more portions. The method further includes directing light onto the nitrided gate oxide layer formations, collecting light reflected from the nitrided gate oxide layer formations and analyzing the reflected light to determine nitrogen concentration of the nitrided gate oxide layer formation. Once the reflected light has been analyzed, the method proceeds to generating feedback information that can be employed in controlling nitrided gate oxide layer formers to regulate nitrided gate oxide formation.

To the accomplishment of the foregoing and related ends, the invention, then, comprises the features hereinafter fully described and particularly pointed out in the claims. The following description and the annexed drawings set forth in detail certain illustrative aspects of the invention. These aspects are indicative of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

Prior Art

FIG. 6 is a perspective illustration of a substrate having a nitrided gate oxide layer deposited thereon in accordance with the present invention.

FIG. 7 is a representative three-dimensional grid map of a nitrided gate oxide layer formation illustrating nitrided gate oxide layer nitrogen concentration measurements taken at grid blocks of the grid map in accordance with the present invention.

FIG. 8 is a nitrided gate oxide layer nitrogen concentration measurement table correlating the gate oxide nitrogen concentration measurements of FIG. 7 with desired values for the nitrogen concentration measurements in accordance with the present invention.

DETAILED DESCRIPTION OF THE INVENTION

Figure 1:
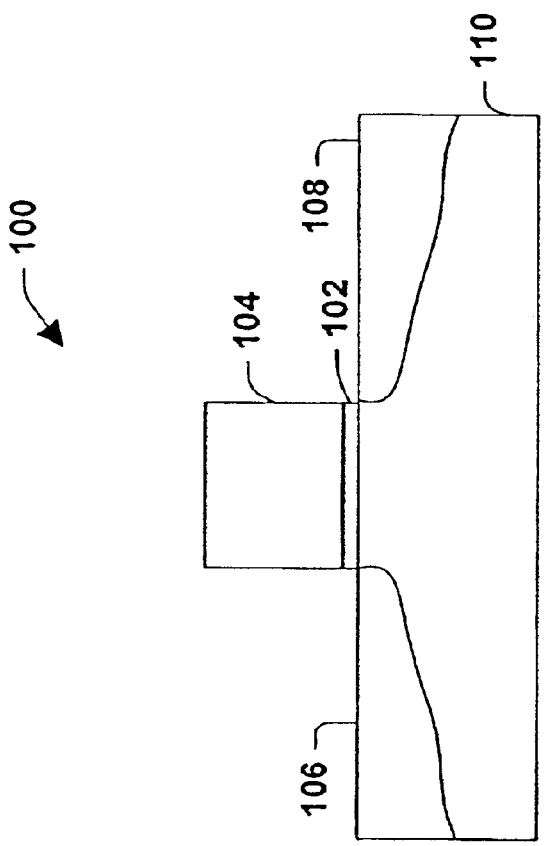
FIG. 1 is a cross section of an exemplary MOSFET device.

The present invention will now be described with reference to the drawings, wherein like reference numerals are used to refer to like elements throughout. The present invention will be described with reference to a system for controlling gate oxide layer formation using one or more gate oxide layer formers and a scatterometry system. It should be understood that the description of these exemplary aspects are merely illustrative and that they should not be taken in a limiting sense.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks may be employed.

The present invention may be used with any of the different types of nitridation processes used for preparing nitrided or stacked gate oxides. The present invention also covers different nitrided interface layers that can be used in high K gate oxides, such as $ZrO_2$ and $HfO_2$ and metal silicates of Hf, Zr, La, etc.

Figure 2:
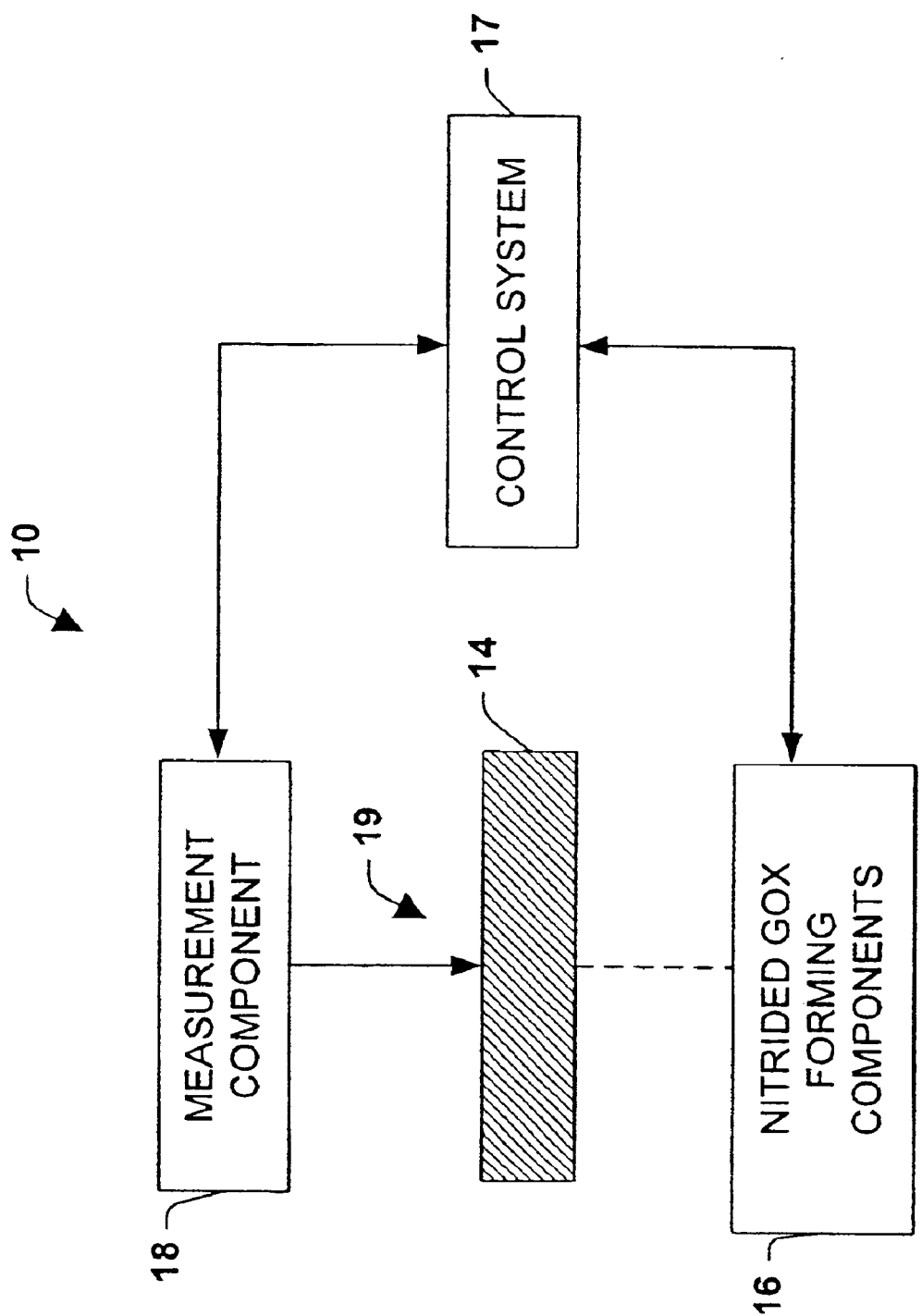
FIG. 2 is a partial schematic block diagram of a gate oxide layer formation monitoring system in accordance with the present invention.

Referring now to FIG. 2, a system 10 for monitoring and controlling nitrogen concentration in nitrided gate oxides on a wafer 14 is shown. One or more nitrided gate oxide (gox) formations may be formed on the wafer 14. The system 10 includes nitrided gox forming components 16 operable to form a nitrided gate oxide on the wafer 14. The system 10 further includes a measurement component 18 operable to measure, in situ, the developing thickness and/or chemical composition of the nitrided gate oxide being formed on the wafer 14 by the nitrided gate oxide forming components 16. The measurement component 18 can direct a light 19 at the wafer 14 and receive light reflected and/or refracted back from the wafer 14. Such reflected and/or refracted light can be analyzed by the measurement component 18, with the results of such analysis passed to a control system 17. The control system 17 can thus be employed to feed forward control information to the nitrided gate oxide components 16, facilitating more precise control of the nitrided gate oxide formed on the wafer 14.

Figure 3:
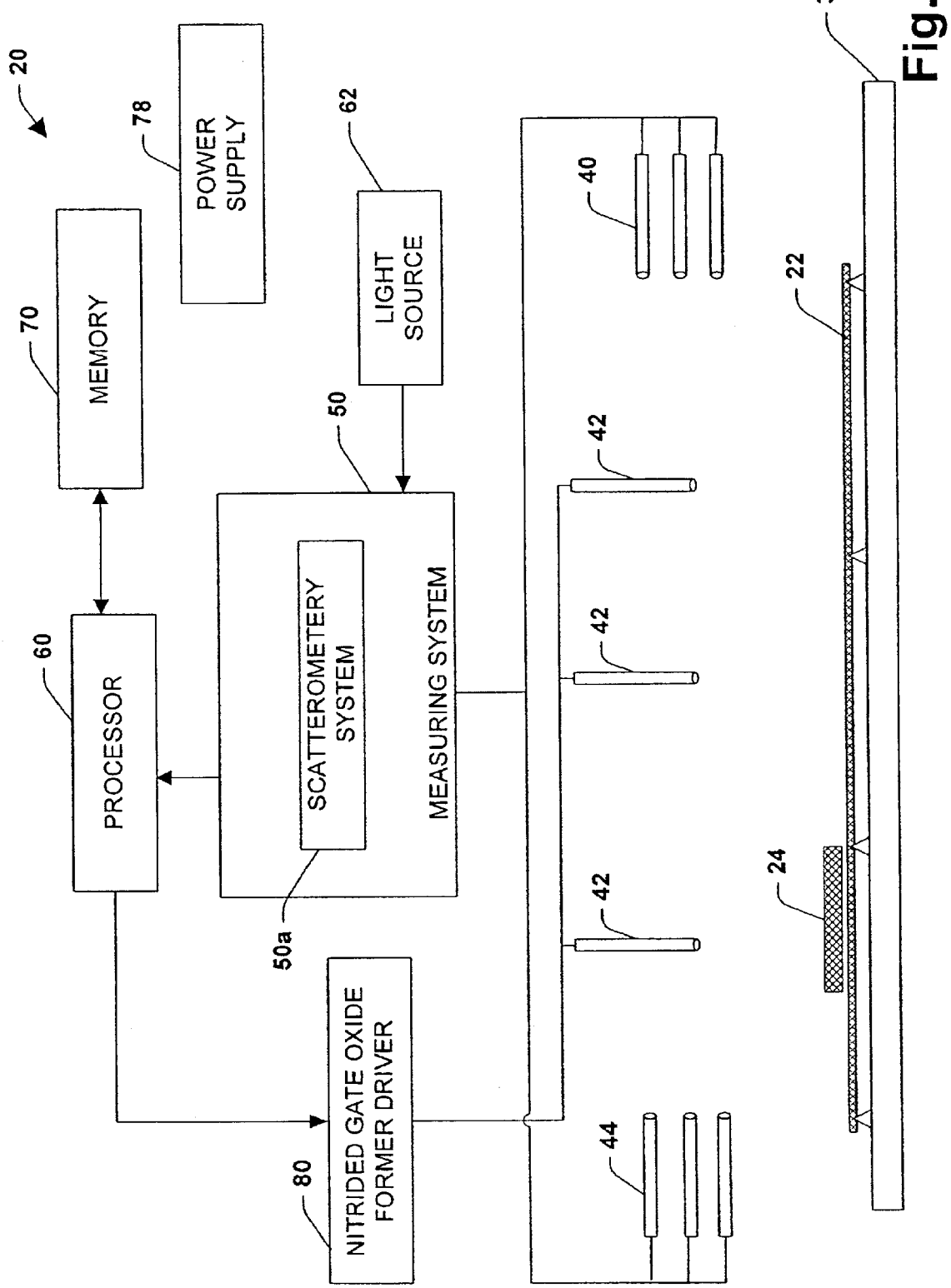
FIG. 3 is schematic block diagram of a gate oxide layer formation monitoring system in accordance with the present invention.

Referring now to FIG. 3, a system 20 for controlling nitrided gate oxide layer formation on a wafer 22 is shown (one or more nitrided gate oxide layer formations 24 may be formed on the wafer 22). It is to be appreciated that a nitrided gate oxide layer formation 24 can be formed from silicon, oxygen and nitrogen containing materials such as one or more materials including, but not limited to, silicon oxide, nitrogen, silicon nitride and silicon oxynitride layers. It is to be further appreciated that such nitrided gate oxide layers can be formed employing techniques including, but not limited to one or more of chemical vapor deposition (CVD), rapid thermal oxidation, oxide growth and annealing in a nitrogen containing compound such as nitric oxide, nitrous oxide, ammonia, and the like The system 20 further includes one or more nitrided gate oxide layer formers 42 that are selectively controlled by the system 20 so as to facilitate controlled formation of nitrided gate oxide layers on the wafer 22. As shown, nitrided gate oxide layer formers 42 are merely representative of apparatus required to make a nitrided gate oxide layer, such as CVD equipment. A detailed illustration of such apparatus is not required for understanding the invention, as such apparatus are known in the art.

One or more light sources 44 project light onto respective portions of the wafer 22. A portion may have one or more nitrided gate oxide layer formations 24 being formed on that portion. Light reflected by the one or more nitrided gate oxide layer formations 24 is collected by one or more light collecting devices 40 and is processed by a nitrided gate oxide layer formation parameter measuring system 50 to measure at least one parameter relating to the nitrogen concentration of the one or more nitrided gate oxide layer formations 24. The reflected through light is processed with respect to the incident light in measuring the various parameters.

The measuring system 50 includes a scatterometry system 50a. It is to be appreciated that any suitable scatterometry system may be employed to carry out the present invention and such systems are intended to fall within the scope of the claims. The scatterometry system 50a can be incorporated into chip manufacturing devices, (e.g., plasma chambers).

A source 62 of light such as a laser, for example, provides light to the one or more light sources 44 via the measuring system 50. Preferably, the light source 62 is a frequency-stabilized laser, however, it will be appreciated that any laser or other light source (e.g., laser diode or helium neon (HeNe) gas laser) suitable for carrying out the present invention can be employed.

A processor 60 receives the measured data from the measuring system 50 and determines the nitrogen concentration of respective nitrided gate oxide layer formations 24 on the portions of the wafer 22. The processor 60 is operatively coupled to system 50 and is programmed to control and operate the various components within the nitrided gate oxide monitoring and controlling system 20 in order to carry out the various functions described herein. The processor, or CPU 60, may be any of a plurality of commercially available processors. The manner in which the processor 60 can be programmed to carry out the functions relating to the present invention will be readily apparent to those having ordinary skill in the art based on the description provided herein. A memory 70, which is operatively coupled to the processor 60, is also included in the system 20 and serves to store program code executed by the processor 60 for carrying out operating functions of the system 20 as described herein. The memory 70 also serves as a storage medium for temporarily storing information such as measured nitrided gate oxide layer nitrogen concentration, desired nitrided gate oxide layer nitrogen concentration, measured nitrided gate oxide layer thickness, desired nitrided gate oxide layer thickness, nitrided gate oxide layer thickness tables, measured nitrided gate oxide layer uniformity, desired nitrided gate oxide layer uniformity, nitrided gate oxide layer tables, wafer coordinate tables, scatterometry information, and other data that may be employed in carrying out the present invention. A power supply 78 provides operating power to the system 20. Any suitable power supply (e.g., battery, line power) may be employed to carry out the present invention.

The processor 60 is also coupled to a nitrided gate oxide former driving system 80 that drives the nitrided gate oxide layer formers 42. The nitrided gate oxide former driving system 80 is controlled by the processor 60 so as to selectively vary output of the respective nitrided gate oxide layer formers 42. Each respective portion of the wafer 22 may have a corresponding nitrided gate oxide former 42 associated therewith. The processor 60 is able to monitor the development of the various nitrided gate oxide layer formations 24 and selectively regulate the nitrogen concentration of each portion via the corresponding nitrided gate oxide layer formers 42. As a result, the system 20 provides for regulating nitrided gate oxide layer formation 24 nitrogen concentration on the wafer 22, which in turn improves, for example, reliability of microprocessor or memory devices and other devices (e.g., any CMOS devices) manufactured employing the present invention. Although not shown, the wafer 22, the nitrided gate oxide layer formations 24, the chuck 30, the light sources 44, the light collecting devices 40 and the gate oxide layer formers 42 may be positioned within a processing chamber wherein certain parameters (e.g., temperature, pressure, gas concentration, atmosphere composition and the like) can be controlled.

Figure 4:
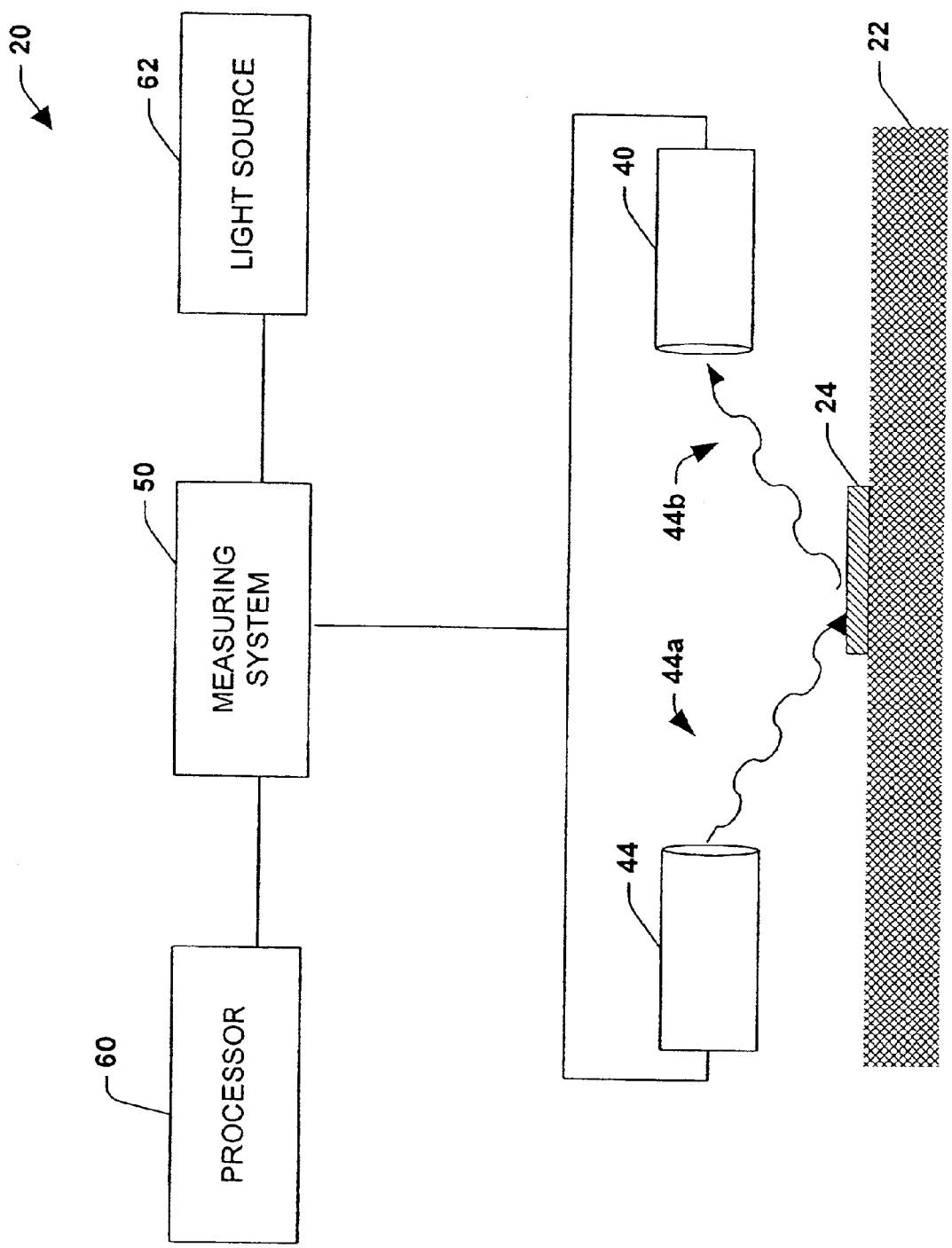
FIG. 4 is a partial schematic block diagram of the system of FIG. 3 being employed in connection with determining the nitrogen concentration of a nitrided gate oxide layer in accordance with the present invention.

FIG. 4 illustrates the system 20 being employed to measure the nitrogen concentration of nitrided gate oxide layer formations 24 on a wafer 22 at a particular location on the wafer. The light source 44 directs a light 44a incident to the surface of the wafer 22, and the angle of a reflected and/or refracted light 44b from the surface of the wafer 22 will vary in accordance with the nitrogen concentration of the nitrided gate oxide layer formation 24. The measuring system 50 collects the light 44b and processes the light 44b in accordance with scatterometry techniques to provide the processor 60 with data corresponding to the nitrogen concentration of the nitrided gate oxide layer formation 24.

Figure 5:
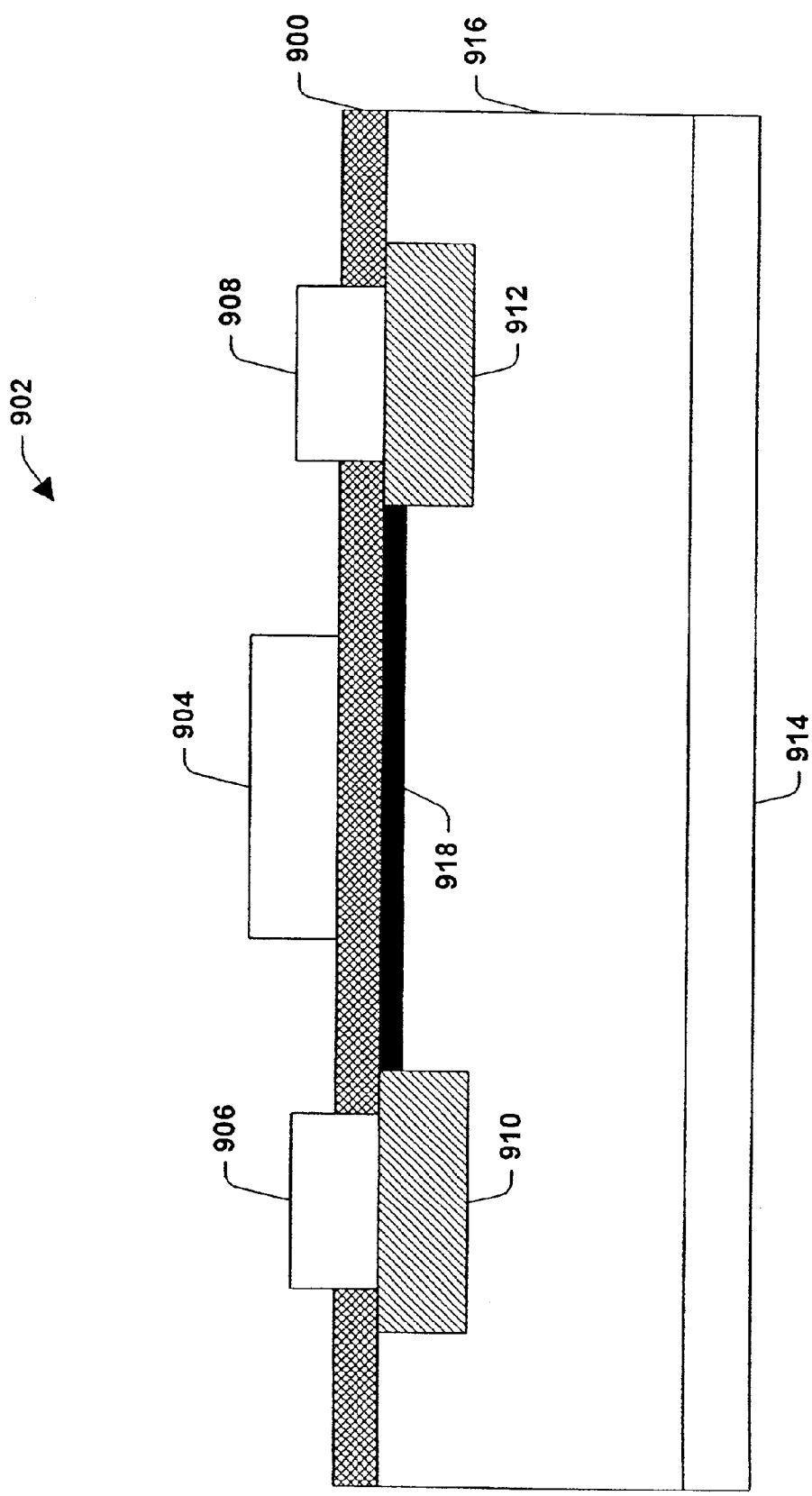
FIG. 5 illustrates a nitrided gate oxide layer in an n-type MOSFET.

FIG. 5 illustrates a nitrided gate oxide layer 900 in an n-type Metal-Oxide-Semiconductor-Field-Effect-Transistor (MOSFET) 902. Precisely controlling the nitrogen concentration of the nitrided gate oxide layer 900 leads to improvements in the reliability of the MOSFET 902. Although FIG. 5 refers primarily to a MOSFET type device, it is to be appreciated that nitrided gate oxide layers formed in accordance with the present invention may be employed in devices including, but not limited to, MOSFETs, EEPROMs (e.g., flash memory), volatile memories (e.g., DRAM, SRAM) and other memory and semiconductor devices. By way of illustration, when employed to monitor and control nitrogen concentration in an interfacial nitridation process, at least two aspects of device reliability and performance can be associated with the quality of the interfacial nitridation. Concerning a MOSFET, improvement of hot-carrier and current-stress reliability is achieved, and second, a reduction of direct and Fowler-Nordheim (F-n) tunneling current is achieved. By way of further illustration, when employed to monitor and control nitrogen concentration in a top-surface nitridation process, improvements in reducing or eliminating B-atom out-diffusion from a $p^+$ gate electrode on a p-mos device with B-doped $p^+$ polycrystalline silicon gate electrodes were achieved. Similarly, additional improvements including eliminating shifts in flat-band voltage (which indicate a reduced interface defect density) are achieved when nitrogen concentration can be precisely controlled in such top-surface nitridation processes. In flash memory devices, reliability of tunnel oxide can be improved.

The present invention facilitates controlling the nitrogen concentration of the nitrided gate oxide layer 900 by collecting scatterometry data associated with the nitrided oxide layer 900 during formation. Data collected during the formation of the nitrided gate oxide layer 900 can thus be analyzed and employed to produce information that can be fed back to control the formation process. For example, if the nitrided gate oxide layer 900 is being formed by thermal oxidation, the analyzed scatterometry data can be employed to generate feedback information operable to control the time over which the oxide growth should continue and/or the temperature at which the continued oxide growth should occur. Alternatively, concentration of nitric oxide, nitrous oxide, or ammonia in the carrier gas can be varied.

The MOSFET 902 includes a gate 904 electrically connected by external wiring (not shown) to a back contact 914. The gate 914 is also electrically connected by wiring (not shown) to a source electrode 906 associated with an n-source 910 and to a drain electrode 908 associated with an n-drain 912. The MOSFET 902 also includes an inversion layer 918 and a p-substrate 916. In the exemplary MOSFET 902 illustrated, the gate oxide 900 is situated between the gate 904 and the inversion layer 918. Reliable operation of the MOSFET 902 can be enhanced by monitoring and controlling the formation of the gate oxide 900 so that a desired nitrogen concentration in the gate oxide 900 is achieved. For example, improvement of hot-carrier and current-stress reliability can be achieved, and direct and Fowler-Nordheim (F-n) tunneling current can be reduced. Similarly, improvements in reducing or eliminating B-atom out-diffusion from a $p^+$ gate electrode on a p-mos device with B-doped $p^+$ polycrystalline silicon gate electrodes can be achieved. Additional improvements including eliminating shifts in flat-band voltage (which indicate a reduced interface defect density) can also be achieved.

Turning now to FIGS. 6–8 the chuck 30 is shown in perspective supporting the wafer 22 whereupon one or more nitrided gate oxide layer formations 24 may be formed. The wafer 22 can be divided into a grid pattern as that shown in FIG. 6. Each grid block (XY) of the grid pattern corresponds to a particular portion of the wafer 22 and each grid block may have one or more nitrided gate oxide layer formations 24 associated with that grid block. Each portion is individually monitored for nitrided gate oxide nitrogen concentration and each portion is individually controlled for nitrided gate oxide formation.

In FIG. 7, each nitrided gate oxide layer formation 24 in each respective portion of the wafer 22 ($X_1Y_1 \ldots X_{12}, Y_{12}$) is being monitored for nitrogen concentration using reflective light, the measuring system 50 and the processor 60. The thickness of each nitrided gate oxide layer formation 24 is shown. The present invention facilitates controlling nitrided gate oxide layer formation 24 nitrogen concentration. An alternative aspect of the present invention facilitates controlling nitrided gate oxide layer formation 24 thickness as a function of nitrogen concentration. As can be seen, the nitrogen concentration at coordinate $X_7Y_6$ is substantially higher than the nitrogen concentration of the other wafer 22 portions XY. It is to be appreciated that although FIG. 7 illustrates the wafer 22 being mapped (partitioned) into 144 grid block portions, the wafer 22 may be mapped with any suitable number of portions and any suitable number of nitrided gate oxide layer formations 24 can be monitored. By way of illustration, a single nitrided gate oxide layer formation 24 may be monitored. By way of further illustration, a single nitrided gate oxide former 42 may be employed. Although the present invention is described with respect to one nitrided gate oxide former 42 corresponding to one grid block XY, it is to be appreciated that any suitable number of nitrided gate oxide layer formers 42 (including a single nitrided gate oxide layer former 42) corresponding to any suitable number of grid blocks (including a single grid block) may be employed. It is to be further appreciated that although FIG. 7 illustrates measurements for nitrided gate oxide formation nitrogen concentration, measurements for thickness and/or uniformity may also be taken.

FIG. 8 is a representative table of nitrogen concentration measurements (taken for the various grid blocks) that have been correlated with acceptable nitrogen concentration values for the portions of the wafer 22 mapped by the respective grid blocks. As can be seen, all the grid blocks, except grid block $X_7Y_6$, have nitrogen concentration measurements corresponding to an acceptable thickness value ($T_A$) (e.g., are within an expected range of thickness measurements), while grid block $X_7Y_6$ has an undesired nitrogen concentration value ($T_U$). Thus, the processor 60 has determined that an undesirable nitrogen concentration condition exists at the portion of the wafer 22 mapped by grid block $X_7Y_6$. Accordingly, the processor 60 can drive the nitrided gate oxide layer former $42_{7,6}$, which corresponds to the portion of the wafer 22 mapped at grid block $X_7Y_6$, to bring the nitrided gate oxide nitrogen concentration of this portion of the wafer 22 to an acceptable level. The present invention thus facilitates precisely controlling the nitrogen concentration of the nitrided gate oxide layer, providing an advantage over conventional systems. It is to be appreciated that the nitrided gate oxide layer formers 42 may be driven so as to maintain, increase and/or decrease the rate of nitrided gate oxide formation of the respective wafer 22 portions as desired. It is to be appreciated that although FIG. 8 illustrates measurements for nitrided gate oxide nitrogen concentration, that measurements for thickness and/or uniformity may also be taken. Such concentration, thickness and uniformity measurements may be employed to generate feedback data to control, in situ, the formation of the nitrided gate oxide layer and particularly to control, in situ, the amount of nitrogen incorporated into the gate oxide layer.

Scatterometry is a technique for extracting information about a surface upon which an incident light has been directed. Information concerning properties including, but not limited to, chemical concentration (e.g., nitrogen concentration) dishing, erosion, profile, thickness of thin films and critical dimensions of features present on the surface can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface (e.g., nitrogen concentration), the planarity of the surface, features on the surface, voids in the surface, and the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N=n-jk$$

where j is an imaginary number.

The signal (signature) library can be constructed from observed intensity/phase signatures and/or signatures generated by modeling and simulation. By way of illustration, when exposed to a first incident light of known intensity, wavelength and phase, a first layer with a first chemical composition on a wafer can generate a first phase/intensity signature. Similarly, when exposed to the first incident light of known intensity, wavelength and phase, a second chemical composition on a wafer can generate a second phase/intensity signature. For example, a nitrided gate oxide layer with a first nitrogen concentration may generate a first signature while a nitrided gate oxide layer with a second nitrogen concentration may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 9:
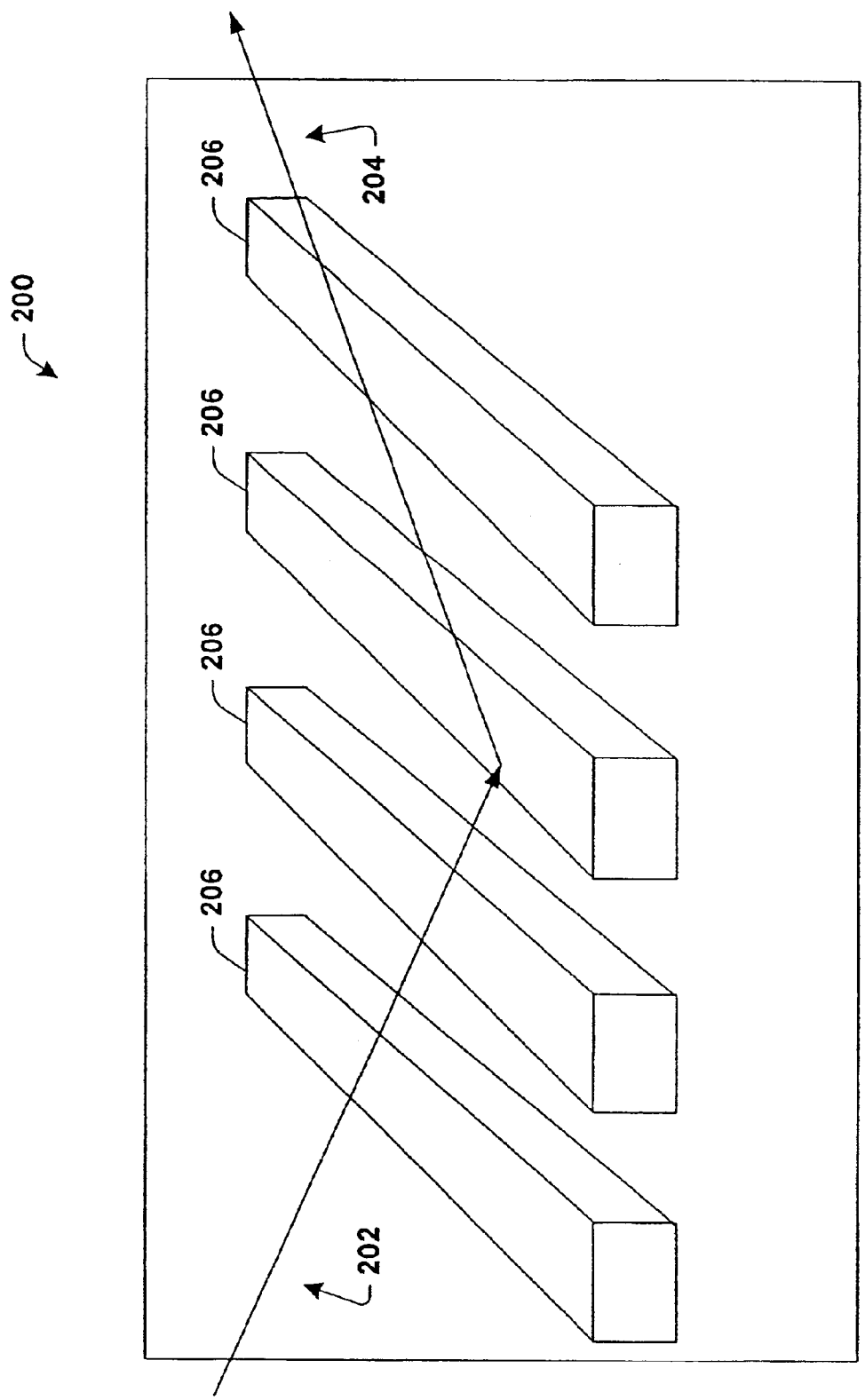
FIG. 9 is a simplified perspective view of an incident light reflecting off a surface, in accordance with an aspect of the present invention.
Figure 14:
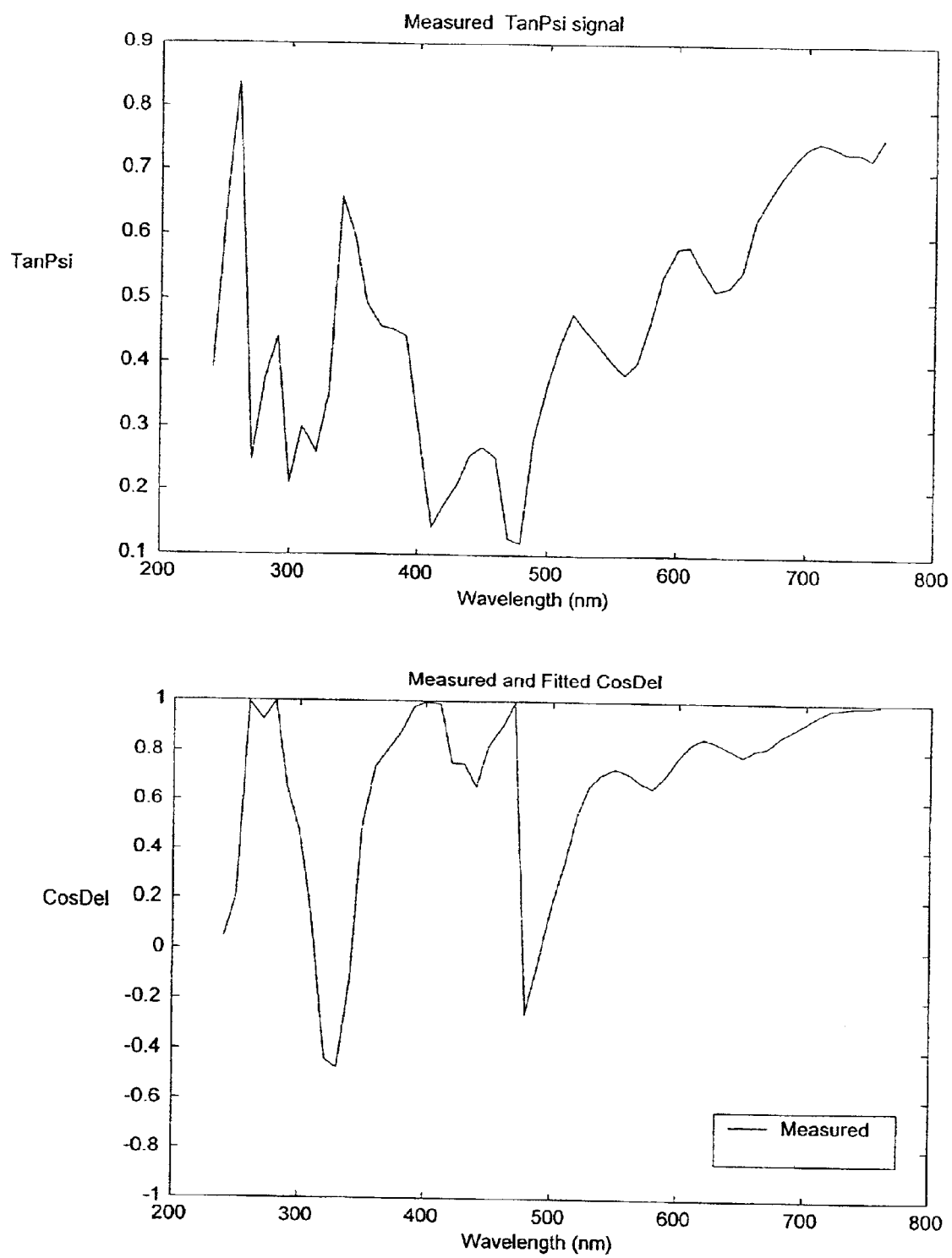
FIG. 14 illustrates phase and intensity signals recorded from a complex reflected and refracted light produced when an incident light is directed onto a surface, in accordance with an aspect of the present invention.

To illustrate the principles described above, reference is now made to FIGS. 9 through 14. Referring initially to FIG. 9, an incident light 202 is directed at a surface 200, upon which one or more features 206 comprised of one or more chemical compositions may exist. In FIG. 9 the incident light 202 is reflected as reflected light 204. The properties of the surface 200, including but not limited to, chemical composition (e.g., nitrogen concentration) thickness, uniformity, planarity and the presence of features, can affect the reflected light 204. In FIG. 9, the features 206 are raised upon the surface 200. The phase and intensity of the reflected light 204 can be measured and plotted, as shown, for example, in FIG. 14. The phase 260 of the reflected light 204 can be plotted, as can the intensity 262 of the reflected light 204. Such plots can be employed to compare measured signals with signatures stored in a signature library using techniques like pattern matching, for example. Although the features 206 are illustrated as substantially regular, it is to be appreciated that irregular features can also be measured using scatterometry techniques.

Figure 10:
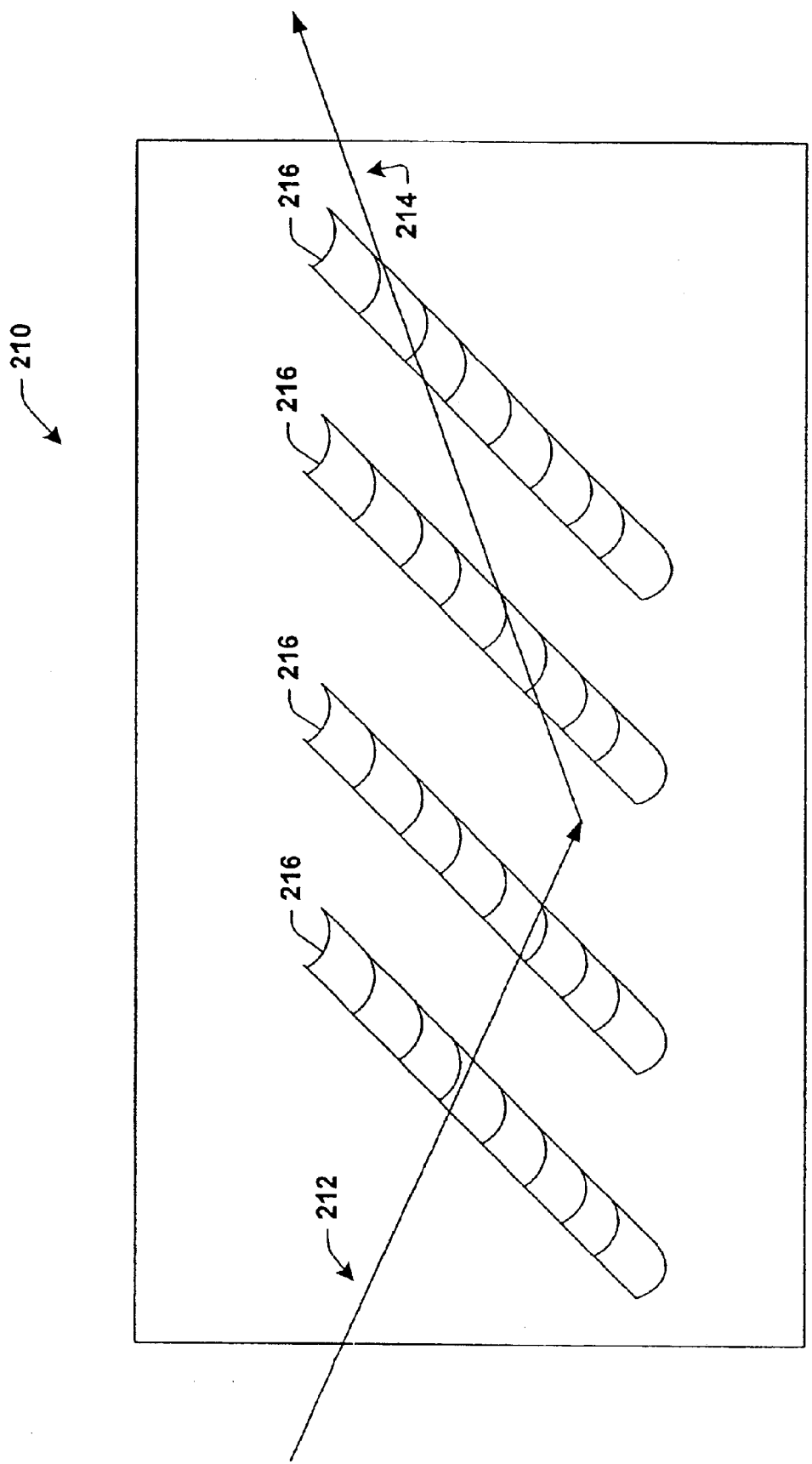
FIG. 10 is a simplified perspective view of an incident light reflecting off a surface, in accordance with an aspect of the present invention.

Referring now to FIG. 10, an incident light 212 is directed onto a surface 210 upon which one or more depressions 216 appear. The incident light 212 is reflected as reflected light 214. Like the one or more features 206 (FIG. 9) may affect an incident beam, so too may the one or more depressions 216 affect an incident beam. For example, a wafer may have multiple layers formed from different chemical compositions. A depression (e.g., 216) may expose a layer with a different chemical composition, which may generate a tell-tale signature. Thus, it is to be appreciated by one skilled in the art that scatterometry can be employed to measure properties of a surface, features appearing on a surface and features appearing in a surface. It is to be further appreciated that the term "features" includes features intentionally and unintentionally appearing on a surface.

Figure 11:
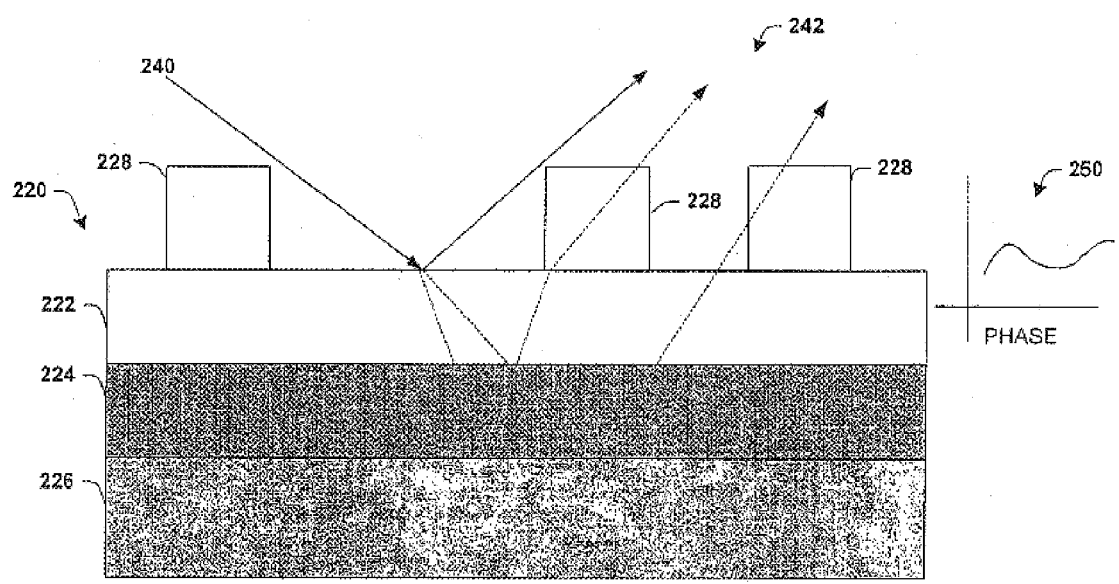
FIG. 11 illustrates a complex reflected and refracted light produced when an incident light is directed onto a surface, in accordance with an aspect of the present invention.

Turning now to FIG. 11, complex reflections and refractions of an incident light 240 are illustrated. The reflection and refraction of the incident light 240 can be affected by factors including, but not limited to, the composition of the substrate 220 upon which the features 228 reside and the presence of one or more features 228. For example, properties of the substrate 220 including, but not limited to the thickness of a layer 222, the chemical properties of the layer 222 (e.g., nitrogen concentration), the opacity and/or reflectivity of the layer 222, the thickness of a layer 224, the chemical properties of the layer 224 (e.g., nitrogen concentration), the opacity and/or reflectivity of the layer 224, the thickness of a layer 226, the chemical properties of the layer 226 (e.g., nitrogen concentration), and the opacity and/or reflectivity of the layer 226 can affect the reflection and/or refraction of the incident light 240. Thus, a complex reflected and/or refracted light 242 may result from the incident light 240 interacting with the features 228, and/or the layers 222, 224 and 226. Although three layers 222, 224 and 226 are illustrated in FIG. 11, it is to be appreciated that a dielectric can be formed of a greater or lesser number of such layers.

Figure 12:
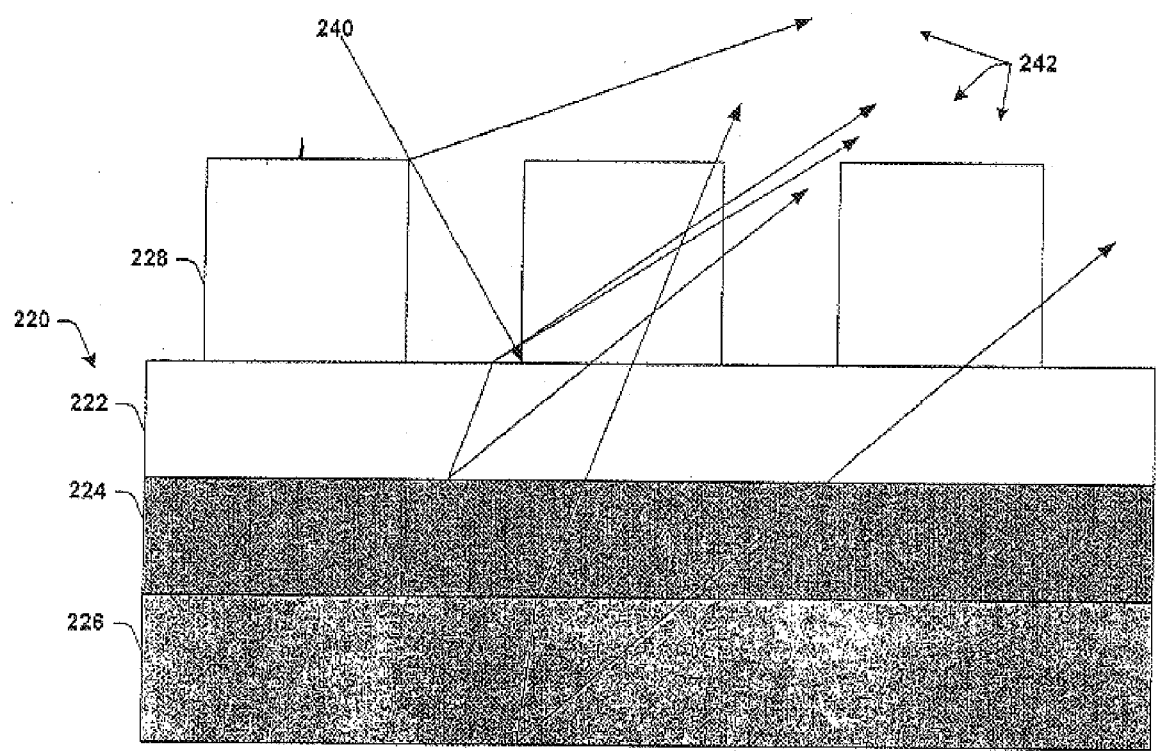
FIG. 12 illustrates a complex reflected and refracted light produced when an incident light is directed onto a surface, in accordance with an aspect of the present invention.
Figure 13:
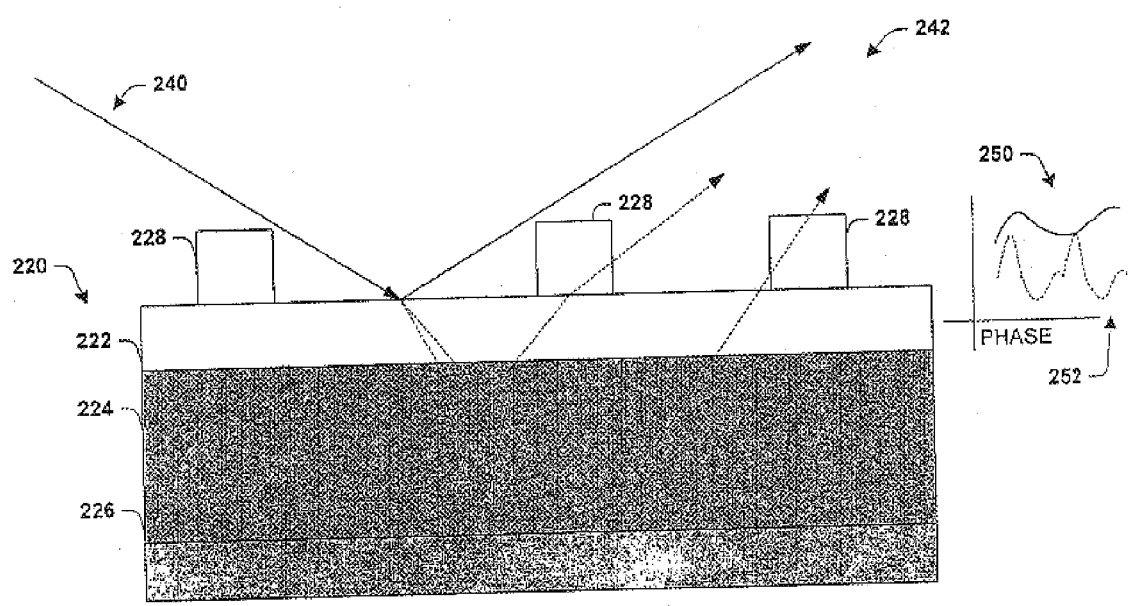
FIG. 13 illustrates a complex reflected and refracted light produced when an incident light is directed onto a surface, in accordance with an aspect of the present invention.

Turning now to FIG. 12, one of the properties from FIG. 11 is illustrated in greater detail. The dielectric 220 can be formed of one or more layers 222, 224 and 226. For example, layer 222 may be an oxide layer, layer 224 may be a nitride layer, and layer 226 may be a nitrided oxide layer. The phase 250 of the reflected and/or refracted light 242 can depend, at least in part, on the nitrogen concentration of the layer 226. Similarly, the phase 250 of the reflected and/or refracted light 242 can depend, at least in part, on the thickness of a layer, for example, the layer 224. Thus, in FIG. 13, the phase 252 of the reflected light 242 differs from the phase 250 due, at least in part, to the different thickness of the layer 224 in FIG. 13. Although the phase is measured and plotted in association with FIGS. 12 and 13, changes to intensity may also be measured and plotted in accordance with the present invention.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Figure 15:
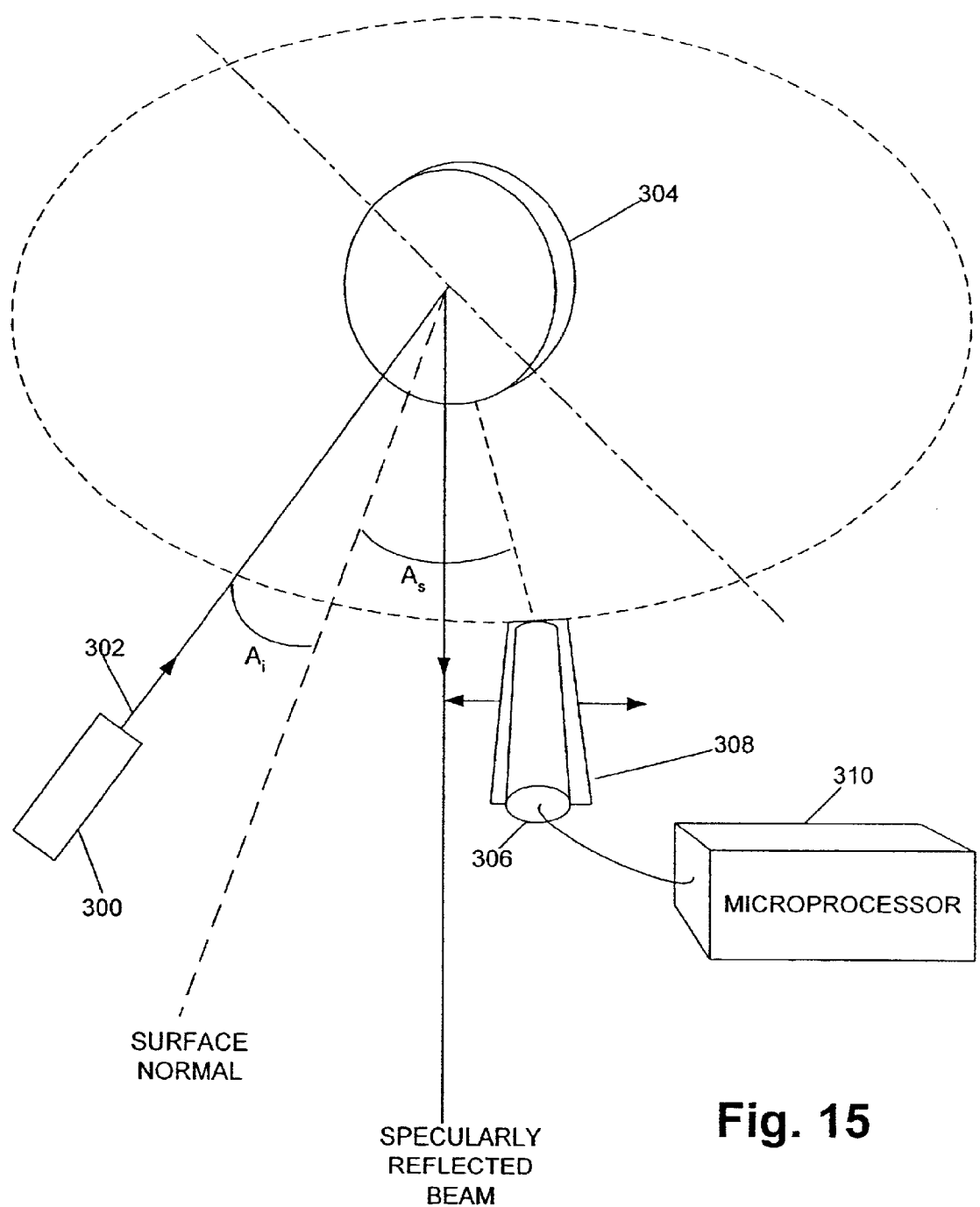
FIG. 15 is an example scatterometry system collecting reflected light in accordance with an aspect of the present invention.

FIG. 15 illustrates an exemplary scatterometry system collecting reflected light. Light from a laser 300 is brought to focus in any suitable well-known manner to form a beam 302. A sample, such as a wafer 304 is placed in the path of the beam 302 and a photo detector or photo multiplier 306 of any suitable well-known construction. Different detector methods may be employed to determine the scattered power. To obtain a grating pitch, the photo detector or photo multiplier 306 may be mounted on a rotation stage 308 of any suitable well-known design. A microprocessor 310, of any suitable well-known design, may be used to process detector readouts, including but not limited to angular locations of different diffracted orders leading to diffraction grating pitches being calculated. Thus, light reflected from the sample 304 may be accurately measured.

Figure 16:
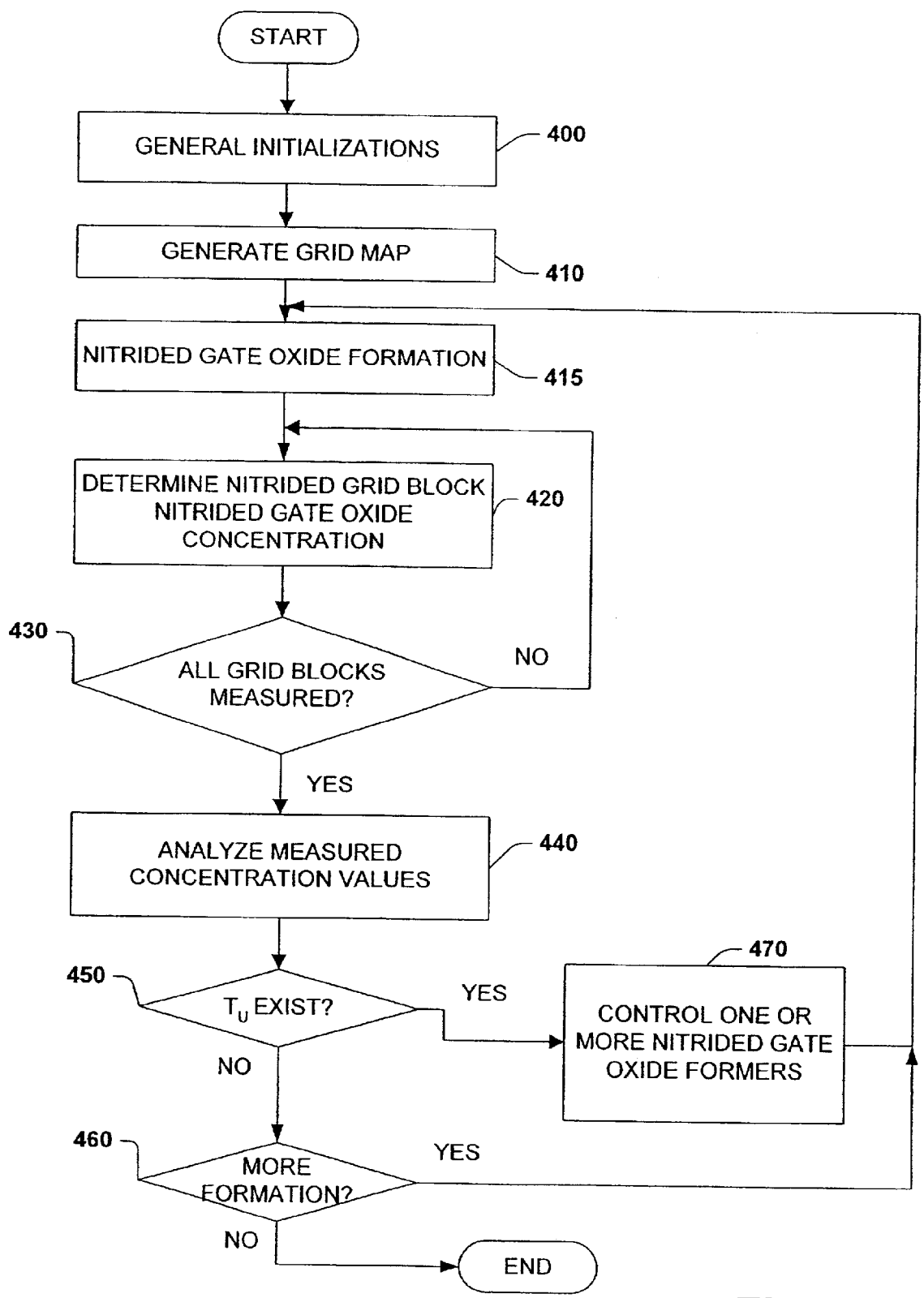
FIG. 16 is a flow diagram illustrating one specific methodology for carrying out the present invention.

In view of the exemplary systems shown and described above, a methodology, which may be implemented in accordance with the present invention, will be better appreciated with reference to the flow diagram of FIG. 16. While, for purposes of simplicity of explanation, the methodology of FIG. 16 is shown and described as a series of blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with the present invention.

FIG. 16 is a flow diagram illustrating one particular methodology for carrying out the present invention. At 400, general initializations are performed. Such initializations can include, but are not limited to, allocating memory, establishing pointers, establishing data communications, initializing variables and instantiating objects. At 410, at least a portion of a wafer is partitioned into a plurality of grid blocks "XY". At 415, at least a part of a nitrided gate oxide layer is formed. For example, a nitrided oxide layer can be formed through oxide growth involving wet thermal oxidation.

At 420, nitrogen concentration determinations are made with respect to the various wafer portions mapped by respective grid blocks XY. Such determinations facilitate controlling, in situ, the amount of nitrogen incorporated into a gate oxide layer, and thus provide an advantage over conventional systems. At 430, a determination is made concerning whether all grid block measurements have been taken. If the determination at 430 is NO, then processing returns to 420. If the determination at 430 is YES, then at 440 the determined nitrogen concentration values are compared to acceptable concentration levels for the respective portions of the wafer. At 450, a determination is made concerning whether any unacceptable nitrogen concentration values exist. If the determination at 450 is NO, that all nitrogen concentration values are acceptable, then at 460 a determination is made concerning whether further formation is required. If the determination at 460 is NO, then processing completes. If the determination at 460 is YES, then processing continues at 415. If the determination at 450 was YES, that unacceptable nitrogen concentration values were found, then at 470 the unacceptable nitrogen concentration values are analyzed. After the analyses of 470, feedback information can be generated to control nitrided gate oxide layer formers corresponding to grid blocks with unacceptable nitrogen concentration values, to regulate characteristics of nitrided gate oxide formation on the respective wafer portions. For example, information concerning the time remaining for nitrided gate oxide formation and/or the temperature at which such nitrided gate oxide formation should occur can be generated. The present iteration is then ended and the process returns to 415 to perform another iteration.

Generating such feedback control information facilitates more precisely controlling the nitrogen concentration of the nitrided gate oxide layer. Such precise control can facilitate achieving desired critical dimensions and in reducing problems (e.g., direct tunneling) associated with ultra-thin gate oxide layers (e.g., less than three nanometers), with resulting increases in semiconductor performance and/or reliability.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for regulating nitrided gate oxide layer formation, comprising:

defining a wafer as a plurality of portions;

establishing one or more nitrided gate oxide layer formations to be formed;

directing light onto at least one of the nitrided gate oxide layer formations;

collecting light reflected from at least one nitrided gate oxide layer formation;

analyzing the reflected light to determine nitrogen concentration of the at least one nitrided gate oxide layer formation; and controlling one or more nitrided gate oxide layer formers to regulate gate oxide formation of the at least one nitrided gate oxide layer formation.

2. The method of claim 1, wherein analyzing the reflected light further comprises:

employing a scatterometry system to process the reflected light.

3. The method of claim 1, further comprising:

collecting light passing through the at least one nitrided gate oxide layer formation; and analyzing the passed through light to determine the nitrogen concentration of the at least one nitrided gate oxide layer formation.

4. The method of claim 1, wherein analyzing the passed through light further comprises:

using a scatterometry system to process the passed through light.

5. The method of claim 1, further comprising:

using a processor to control the at least one nitrided gate oxide former based at least partially on data received from the scatterometry system.

6. The method of claim 4, further comprising:

using a processor to control the at least one nitrided gate oxide former based at least partially on data received from the scatterometry system.

7. A method for regulating nitrided gate oxide layer formation, comprising:

partitioning a wafer into a plurality of grid blocks;

using one or more nitrided gate oxide layer formers to form one or more nitrided gate oxide layers on the wafer, each nitrided gate oxide former functionally corresponding to a respective grid block;

determining nitrogen concentration of the one or more nitrided gate oxide layer formations on one or more portions of the wafer, each portion corresponding to a respective grid block; and using a processor to coordinate control of the nitrided gate oxide layer formers, respectively, in accordance with determined nitrided gate oxide nitrogen concentration of the respective portions of the wafer.

8. A method for regulating nitrided gate oxide layer formation, comprising:

defining a wafer as a plurality of portions;

establishing one or more nitrided gate oxide layer formations to be formed;

directing light onto at least one of the nitrided gate oxide layer formations;

collecting light reflected from at least one nitrided gate oxide layer formation;

analyzing the reflected light to determine nitrogen concentration of the at least one nitrided gate oxide layer formation;

controlling one or more nitrided gate oxide layer formers to regulate gate oxide formation of the at least one nitrided gate oxide layer formation;

collecting light passing through the at least one nitrided gate oxide layer formation; and analyzing the passed through light to determine the nitrogen concentration of the at least one nitrided gate oxide layer formation.

9. The method of claim 8, wherein analyzing the reflected light further comprises:

employing a scatterometry system to process the reflected light.

10. The method of claim 8, wherein analyzing the passed through light further comprises:

using a scatterometry system to process the passed through light.

11. The method of claim 8, further comprising:

using a processor to control the at least one nitrided gate oxide former based at least partially on data received from the collected light.

12. The method of claim 10, further comprising:

using a processor to control the at least one nitrided gate oxide former based at least partially on data received from the scatterometry system.

13. The method of claim 8, wherein the nitrided gate oxide layer has a thickness of less than ten nanometers.

14. The method of claim 8, wherein the nitrided gate oxide layer has a thickness of less than three nanometers.

15. A method for regulating nitrided gate oxide layer formation, comprising:

defining a wafer as a plurality of portions;

establishing one or more nitrided gate oxide layer formations to be formed;

directing light onto at least one of the nitrided gate oxide layer formations;

collecting light reflected from at least one nitrided gate oxide layer formation;

analyzing the reflected light to determine nitrogen concentration of the at least one nitrided gate oxide layer formation using a scatterometry system;

controlling one or more nitrided gate oxide layer formers to regulate gate oxide formation of the at least one nitrided gate oxide layer formation; and using a processor to control the at least one nitrided gate oxide former based at least partially on data received from the scatterometry system.

16. The method of claim 15, wherein analyzing the reflected light further comprises:

employing a scatterometry system to direct light onto at least one of the nitrided gate oxide layer formations.

17. The method of claim 15, further comprising:

collecting light passing through the at least one nitrided gate oxide layer formation; and analyzing the passed through light to determine the nitrogen concentration of the at least one nitrided gate oxide layer formation.

18. The method of claim 15, wherein the nitrided gate oxide layer has a thickness of less than three nanometers.

19. The method of claim 15, wherein the nitrided gate oxide layer has a thickness of less than ten nanometers.

* * * * *